United States Patent
Evans

(10) Patent No.: US 12,239,720 B2
(45) Date of Patent: Mar. 4, 2025

(54) COMPOSITIONS FOR USE IN LYSIS OF SELECTIVE CANCER CELLS

(71) Applicant: ONCOLYZE, INC., New York, NY (US)

(72) Inventor: Steven Evans, New York, NY (US)

(73) Assignee: Oncolyze, Inc., New York, NY (US)

(*) Notice: Subject to any disclaimer, the term of this patent is extended or adjusted under 35 U.S.C. 154(b) by 0 days.

(21) Appl. No.: 17/045,620

(22) PCT Filed: Apr. 8, 2019

(86) PCT No.: PCT/US2019/026390
§ 371 (c)(1),
(2) Date: Oct. 6, 2020

(87) PCT Pub. No.: WO2019/195851
PCT Pub. Date: Oct. 10, 2019

(65) Prior Publication Data
US 2021/0128754 A1    May 6, 2021

Related U.S. Application Data

(60) Provisional application No. 62/653,808, filed on Apr. 6, 2018.

(51) Int. Cl.
| | |
|---|---|
| A61K 38/03 | (2006.01) |
| A61K 38/10 | (2006.01) |
| A61K 38/16 | (2006.01) |
| A61K 38/17 | (2006.01) |
| A61K 49/14 | (2006.01) |
| A61P 35/00 | (2006.01) |

(52) U.S. Cl.
CPC .............. *A61K 49/14* (2013.01); *A61K 38/10* (2013.01); *A61K 38/17* (2013.01); *A61P 35/00* (2018.01)

(58) Field of Classification Search
CPC ................................ A61K 38/17; A61P 35/00
See application file for complete search history.

(56) References Cited

U.S. PATENT DOCUMENTS

| | | |
|---|---|---|
| 5,519,118 A | 5/1996 | Vogelstein et al. |
| 5,550,023 A | 8/1996 | Kinzler et al. |
| 5,618,921 A | 4/1997 | Burrell et al. |
| 5,702,908 A | 12/1997 | Picksley et al. |
| 5,770,377 A | 6/1998 | Picksley et al. |
| 6,063,911 A | 5/2000 | Vournakis et al. |
| 6,153,391 A | 11/2000 | Picksley et al. |
| 6,310,040 B1 | 10/2001 | Bozyczko-Coyne et al. |
| 6,326,464 B1 | 12/2001 | Conseiller et al. |
| 6,492,116 B1 | 12/2002 | Chene et al. |
| 6,617,346 B1 | 9/2003 | Kong et al. |
| 6,734,302 B2 | 5/2004 | Kong et al. |
| 6,784,157 B2 | 8/2004 | Halazonetis et al. |
| 6,897,197 B2 | 5/2005 | Depinho |
| 6,962,792 B1 | 11/2005 | Ball et al. |
| 7,083,983 B2 | 8/2006 | Lane et al. |
| 7,132,421 B2 | 11/2006 | Fotouhi et al. |
| 7,138,236 B1 | 11/2006 | Jackson et al. |
| 7,173,006 B2 | 2/2007 | Mukherjee et al. |
| 7,241,738 B2 | 7/2007 | Averback et al. |
| 7,531,515 B2 | 5/2009 | Pincus |
| 7,745,405 B2 | 6/2010 | Pincus |
| 7,883,888 B2 | 2/2011 | Michl |
| 8,822,419 B2 | 9/2014 | Pincus et al. |
| 2002/0031818 A1 | 3/2002 | Ronai et al. |
| 2002/0077283 A1 | 6/2002 | Sessa |
| 2002/0098581 A1 | 7/2002 | Glassy et al. |
| 2003/0104622 A1 | 6/2003 | Robbins et al. |
| 2003/0109437 A1 | 6/2003 | Averback et al. |
| 2004/0038902 A1 | 2/2004 | Pincus |
| 2004/0110690 A1 | 6/2004 | Bonny |
| 2005/0090646 A1 | 4/2005 | Sullivan |
| 2005/0137137 A1 | 6/2005 | Lane et al. |
| 2005/0215548 A1 | 9/2005 | Wang et al. |
| 2005/0245451 A1 | 11/2005 | Pincus |
| 2006/0105956 A1 | 5/2006 | Pincus et al. |
| 2006/0211757 A1 | 9/2006 | Wang et al. |
| 2006/0258841 A1 | 11/2006 | Michl et al. |

(Continued)

FOREIGN PATENT DOCUMENTS

| | | |
|---|---|---|
| EP | 2311814 A1 | 4/2011 |
| WO | 98/47919 A1 | 10/1998 |

(Continued)

OTHER PUBLICATIONS

National Institute of Cancer—understanding and related topics, accessed Aug. 21, 2014 at URL: cancer.gov/cancertopics/understandingcancer, 63 pages (Year: 2014).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*
Merck Manuals Neuroblastoma accessed Mar. 12, 2017 at URL merckmanuals.com/professional/pediatrics/pediatric-cancers/neuroblastoma, 4 pages (Year: 2017).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2014).*

(Continued)

*Primary Examiner* — Julie Ha
*Assistant Examiner* — Kristina M Hellman
(74) *Attorney, Agent, or Firm* — Hoffmann & Baron, LLP

(57) ABSTRACT

The present invention relates to a method of necrosing, causing membranolysis, or causing poration of selective cancer cells. In some aspects, the method includes administering a peptide including PPLSQETFSDLWKLLKKWKMRRNQFWVKVQRG (SEQ ID NO:48) or ETFSDLWKLLKKWKMRRNQFWVKVQRG (SEQ ID NO:49) to a selective cancer cell to cause necrosis, membranolysis, or poration of said selective cancer cell.

4 Claims, 1 Drawing Sheet

Specification includes a Sequence Listing.

(56) References Cited

U.S. PATENT DOCUMENTS

| | | |
|---|---|---|
| 2007/0238666 A1 | 10/2007 | Pincus |
| 2008/0070853 A1 | 3/2008 | Michl et al. |
| 2008/0076713 A1 | 3/2008 | Pincus |
| 2010/0143358 A1 | 6/2010 | Weisbart |
| 2011/0183915 A1* | 7/2011 | Pincus .............. C07K 14/4746 435/375 |
| 2015/0094271 A1 | 4/2015 | Lee et al. |
| 2017/0057999 A1* | 3/2017 | Pincus .................. C07K 14/00 |
| 2018/0016302 A1 | 1/2018 | Pincus |

FOREIGN PATENT DOCUMENTS

| | | |
|---|---|---|
| WO | 03/105880 A1 | 12/2003 |
| WO | 2005123676 A1 | 12/2005 |
| WO | WO2009070650 A1 | 6/2009 |
| WO | WO2010040051 A2 | 4/2010 |

OTHER PUBLICATIONS

Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages (Year: 2017).*

Thyroid cancer accessed Mar. 12, 2017 at URL www.merckmanuals.com/professional/endocrine-and-metabolic-disorders/thyroid-disorders/thyroid-cancers, 4 pages (Year: 2017).*

Renal cell carcinoma, accessed Mar. 12, 2017 at URL merckmanuals.com/professional/genitourinary-disorders/genitourinary-cancer/renal-cell-carcinoma, 6 pages (Year: 2017).*

Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*

Merck Manual overview of Leukemia accessed Aug. 21, 2014 at URL: merckmanuals.com/home/blood_disorders/leukemias/overview_of_leukemia.html , 2 pages (Year: 2014).*

Davitt et al, "The Anti-Cancer Peptide, PNC-27, Induces Tumor Cell Necrosis of a Poorly Differentiated Non-Solid Tissue Human Leukemia Cell Line that Depends on Expression of HDM-2 in the Plasma Membrane of these Cells," Annals of Clinical & Laboratory Science 44: 241-248 (2014) (Year: 2014).*

Kanovsky et al., "Peptides from the amino terminal mdm-2-binding domain of p53, designed from conformational analysis, are selectively cytotoxic to transformed cells," PNAS 98: 12438-12443 (2001) (Year: 2001).*

Hu, "Epigenetics of hematopoiesis and hematological malignancies," genes and development 30: 2021-2041 (2016) (Year: 2016).*

Barak et al., "Clinical utility of cytokeratins as tumor markers," Clinical Biochemistry 37: 529-540 (2004) (Year: 2004).*

Abdelaal et al., "MDM2 Expression in Serous and Mucinous Epithelial Tumours of the Ovary", Asian Pac J. Cancer Prev., vol. 17, Iss. 7, pp. 3295-3300 (Jul. 2016).

Gradiz et al., "MIA PaCa-2 and PANC-1—Pancreas Ductual Adenocarcinoma Cell Lines with Neuroendocrine Differentiation and Somatostatin Receptors", Scientific Reports, vol. 6, pp. 1-14 (Feb. 2016).

Leite et al., "Abnormal Expression of MDM2 in Prostate Carcinoma", Modern Pathology, vol. 14, No. 5, pp. 428-436 (May 2001).

Nagata et al., "Structural Basis for Inhibition of the MDM2:p53 Interaction by an Optimized MDM2-Binding Peptide Selected with mRNA Display", PLoS One, vol. 9, Iss. 10, pp. 1-9 (Oct. 2014).

Swetzig et al., "Estrogen Receptor Alpha (ERα/ESR1) Mediates the p53-Independent Overexpression of MDM4/MDMX and MDM2 in Human Breast Cancer", Oncotarget, vol. 7, No. 13, pp. 16049-16069 (Feb. 2016).

International Search Report for corresponding PCT application PCT/US2019/026390, pp. 1-4 (Aug. 2019).

Futaki, Shiroh et al., "Arginine-rich peptides an abundant source of membrane-permeable peptides having potential as carriers for intracellular protein delivery", The Journal of Biological Chemistry, vol. 276, No. 8, issue of Feb. 23, pp. 5836-5840, 2001.

Okuyama, Masahiro et al., "Small-molecule mimics of an a-helix for efficient transport of proteins into cells", Nature vol. 4, No. 2, pp. 153-159, 2007.

Bowne, Wilbur B., et al., "Novel peptides from the RAS-p21 and p53 proteins for the treatment of cancer", NIH Public vol. 5B, pp. 331-344, 2007.

Schaschke, N., et al., "Epoxysuccinyl peptide-derived cathepsin B inhibitors: modulating membrane permeability by conjugation with the C-terminal heptapeptide segment of penetratin", Biological Chemistry, vol. 383, No. 5, pp. 849-852, 2002. (abstract).

Fischer, Peter M., et al., "Small-molecule inhibitors of the p53 suppressor HDM2: have protein-protein interactions of age as drug targets?", Trends in Pharmacological Sciences, vol. 25, No. 7, pp. 343-346, 2004.

Wasylyk, Christine et al., "p53 mediated death of cells overexpressing MDM2 by an inhibitor of MDM2 interaction p53", Oncogene, vol. 18, pp. 1921-1934, 1999.

Cordenonsi, Michelangelo, et al., "Integration of TGF-β and Ras/MAPK signaling through p53 phosphorylation." Science 315.5813 (2007): 840-843.

Shinohara, Kunio et al., "Apoptosis induction resulting from proteasome inhibition", Biochemical Journal, vol. 317, 385-388, 1996.

Kojima, Kensuke et al., "Mdm2 inhibitor nutlin-3a induces p53-mediated apoptosis by transcription-dependent and transcription-independent mechanisms and may overcome atm-mediated resistance to fludarabine in chronic lymphocytic leukemia", Blood, vol. 108, No. 3, pp. 993-1000, 2006.

Alarcon-Vargas, Dania et al., "p53-Mdm2—the affair that never ends", Carcinogenesis, vol. 23, No. 4, pp. 541-547, 2002.

De Graaf, Petra et al., "HdmX protein stability is regulated by the ubiquitin ligase", The Journal of Biological Chemistry, vol. 278, No. 40, issue of Oct. 3, pp. 38315-38324, 2003.

Moll, Ute M., et al., "The MDM2-p53 interaction", Molecular Cancer Research, vol. 1, pp. 1001-1008, 2003.

Patton, John T., et al., "Levels of HdmX expression dictate the sensitivity of normal and transformed cells to nutlin-3", Cancer Research 2006, vol. 66, No. 6, pp. 3169-3176, 2006.

Rohr, Kerstin B., et al., "X-ray structures of free and leupeptin-complexed human al-tryptase mutants: indication for an α→β-tryptase transition", Journal of Molecular Biology, vol. 357, pp. 195-209, 2006.

Moldoveanu, T., et al., "Crystal structures of calpain-E64 and -leupeptin inhibitor complexes reveal mobile loops gating the active site", Journal of Molecular Biology, vol. 343, pp. 1313-1326, 2004.

Vassilev, Lyubomir T. et al., "In vivo activation of the p53 pathway by small-molecule antagonists of MDM2", Science, vol. 303, No. 844, DOI: 10.1126/science.1092472, 2004.

Vassilev, Lyubomir T., et al., "Selective small-molecule inhibitor reveals critical mitotic functions of human CDK1", PNAS, vol. 103, No. 28, pp. 10660-10665, 2006.

Virkajarvi et al., "Association between p53 overexpression, cell proliferation, tumor necrosis and extent of apoptosis in operated pancreatic adenocarcinoma", APMIS, 105; 765-772, 1997.

Vassilev, Lyubomir T., "p53 Activation by Small Molecules: Application in Oncology", J Medicine Chemistry 2005 vol. 48, No. 14, pp. 4491-4499.

Xu et al., "Phase II Trial of a 2h Infusion of Gemcitabine Plus Carboplatin as First-Line Chemotherapy for Advanced Non-Small-Cell Lung Cancer," Cancer Chemother Pharmacol, vol. 59, pp. 1-7 (2007).

Keene, Nancy, "Childhood Leukemia: A Guide for Families, Friends & Caregivers," Childhood Cancer Guides, Chapter 2, pp. 13-17 (2010).

Knepper, Todd C., et al., "Novel and Expanded Oncology Drug Approvals of 2016—Part 1: New Options in Solid Tumor Management," Oncology, vol. 31, No. 2, pp. 110-121 (Williston Park, NY 2017).

Knepper, Todd C., et al., "Novel and Expanded Oncology Drug Approvals of 2016—Part 2: New Options in the Management of Hematologic Malignancies," Oncology, vol. 31, No. 2, pp. 138-146 (Williston Park, NY 2017).

(56) References Cited

OTHER PUBLICATIONS

Smith, B. Douglas, et al., "Meaningful Endpoints for Therapies Approved for Hematologic Malignancies," Cancer vol. 123, No. 10, pp. 1689-1694 (2017).
Saultz, Jennifer N., et al., "Acute Myeloid Leukemia: A Concise Review," Journal of Clinical Medicine, vol. 5, No. 3, p. 33 (2016).
Jabbour, Elias, et. al., "Chronic Myeloid Leukemia: 2016 Update on Diagnosis, Therapy, and Monitoring," American Journal of Hematology, vol. 91, No. 2, pp. 252-265 (2016).
Evers, Dorothea, et al., "Treatments for Hematologic Malignancies in Contrast to Those for Solid Cancers are Associated with Reduced Red Cell Alloimmunization," Haematologica, vol. 102, No. 1, pp. 52-59 (2017).
Wergeland, Line, et al., "Pre-Apoptotic Response to Therapeutic DNA Damage Involves Protein Modulation of Mcl-1, Hdm2 and Flt3 in Acute Myeloid Leukemia Cells," Molecular Cancer, vol. 6, No. 1, pp. 1-11 (2007).
Wang, Huafeng, et al., "Targeting Cell Membrane HDM2: A Novel Therapeutic Approach for Acute Myeloid Leukemia," Leukemia, vol. 34, No. 1, pp. 75-86 (2020).
Weisberg, Ellen, et al., "Inhibition of Wild-Type p53-Expressing AML by the Novel Small Molecule HDM2 Inhibitor CGM097CGM097: Novel Treatment for AML," Molecular Cancer Therapeutics, vol. 14, No. 10, pp. 2249-2259 (2015).
Wang, Huafeng, et al. "PNC-27 Targeting Plasma Membrane HDM2: A Potentially Novel Therapeutic Approach for Acute Myeloid Leukemia (AML)." Blood 130 (2017): 2518.
Sarafraz-Yazdi, Ehsan, et al. "Anticancer peptide PNC-27 adopts an HDM-2-binding conformation and kills cancer cells by binding to HDM-2 in their membranes." Proceedings of the National Academy of Sciences 107.5 (2010): 1918-1923.

\* cited by examiner

SEQUENCE LISTING

```
<160> NUMBER OF SEQ ID NOS: 56

<210> SEQ ID NO 1
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 1

Pro Pro Leu Ser Gln Glu Thr Phe Ser Asp Leu Trp Lys Leu Leu
1               5                   10                  15

<210> SEQ ID NO 2
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 2

Glu Thr Phe Ser Asp Leu Trp Lys Leu Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 3

Met Pro Arg Phe Met Asp Tyr Trp Glu Gly Leu Asn
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 4

Val Gln Asn Phe Ile Asp Tyr Trp Thr Gln Gln Phe
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic Sequence
```

```
<400> SEQUENCE: 5

Thr Gly Pro Ala Phe Thr His Tyr Trp Ala Thr Phe
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 6

Ile Asp Arg Ala Pro Thr Phe Arg Asp His Trp Phe Ala Leu Val
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 7

Pro Arg Pro Ala Leu Val Phe Ala Asp Tyr Trp Glu Thr Leu Tyr
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 8

Pro Ala Phe Ser Arg Phe Trp Ser Asp Leu Ser Ala Gly Ala His
1               5                   10                  15

<210> SEQ ID NO 9
<211> LENGTH: 10
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 9

Pro Xaa Phe Xaa Asp Tyr Trp Xaa Xaa Leu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 10
```

```
Gln Pro Thr Phe Ser Asp Tyr Trp Lys Leu Leu Pro
1               5                   10
```

```
<210> SEQ ID NO 11
<211> LENGTH: 15
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 11

Pro Pro Leu Thr Ser Phe Xaa Glu Tyr Trp Ala Leu Leu Xaa Pro
1               5                   10                  15
```

```
<210> SEQ ID NO 12
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 12

Pro Pro Leu Ser Gln Thr Ser Phe Ala Glu Tyr Trp Asn Leu Leu
1               5                   10                  15
```

```
<210> SEQ ID NO 13
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 13

Leu Thr Phe Glu His Tyr Trp Ala Gln Leu Thr Ser
1               5                   10
```

```
<210> SEQ ID NO 14
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 14

Thr Ser Phe Ala Glu Tyr Trp Asn Leu Leu Ser Pro
1               5                   10
```

```
<210> SEQ ID NO 15
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 15

Gln Glu Thr Phe Ser Asp Leu Trp Lys Leu Leu Pro
1               5                   10
```

```
<210> SEQ ID NO 16
```

```
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 16

Met Pro Arg Phe Met Asp Tyr Trp Glu Gly Leu Asn
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 17

Gln Gln Met His Leu Met Ser Tyr Ala Pro Gly Pro
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 18

Thr Ile Arg Pro Ser Thr Thr Met Asp Ser Pro Thr
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 19

Tyr Ala Asn Pro Gln Met Glu Lys Ala Phe Glu Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 20

Leu Thr Phe Glu His Tyr Trp Ala Gln Leu Thr Ser
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 21

Leu Pro Asn Leu Thr Trp Ala Leu Met Pro Gly Ala
1               5                   10

<210> SEQ ID NO 22
<211> LENGTH: 12
```

```
<212> TYPE: PRT
<213> ORGANISM: Artificial Sequence
<220> FEATURE:
<223> OTHER INFORMATION: Synthetic Sequence

<400> SEQUENCE: 22

Tyr Ala Asn Pro Gln Met Glu Lys Ala Phe Ala Ser
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 23

Leu Thr Phe Glu His Tyr Trp Ala Gln Leu Thr Ser
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 24

Leu Leu Ala Asp Thr Thr His His Arg Pro Trp Thr
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 25

Lys Lys Trp Lys Met Arg Arg Asn Gln Phe Trp Val Lys Val Gln Arg
1               5                   10                  15

Gly

<210> SEQ ID NO 26
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 26

Met Pro Phe Ser Thr Gly Lys Arg Ile Met Leu Gly Glu
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 27

Tyr Gly Arg Lys Lys Arg Arg Gln Arg Arg Pro Pro Gln
1               5                   10

<210> SEQ ID NO 28
```

```
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 28

Gly Arg Lys Lys Arg Arg Gln Arg Arg Arg Pro Pro Gln
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 29

Gly Ala Ala Ala Ala Ala Ala Ala Ala Ala Pro Pro Gln
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 30

Pro Lys Lys Lys Arg Lys Val
1               5

<210> SEQ ID NO 31
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 31

Lys Arg Pro Ala Ala Ile Lys Lys Ala Gly Gln Ala Lys Lys Lys Lys
1               5                   10                  15

<210> SEQ ID NO 32
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 32

Thr Arg Gln Ala Arg Arg Asn Arg Arg Arg Arg Trp Arg Glu Arg Gln
1               5                   10                  15

Arg

<210> SEQ ID NO 33
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 33

Arg Arg Arg Arg Asn Arg Thr Arg Arg Asn Arg Arg Arg Val Arg
1               5                   10                  15
```

```
<210> SEQ ID NO 34
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 34

Lys Met Thr Arg Ala Gln Arg Arg Ala Ala Arg Arg Asn Arg Trp
1               5                   10                  15

Thr Ala Arg

<210> SEQ ID NO 35
<211> LENGTH: 13
<212> TYPE: PRT
<213> ORGANISM: Artificial Sequence
<220> FEATURE:
<223> OTHER INFORMATION: Synthetic Sequenc

<400> SEQUENCE: 35

Thr Arg Arg Gln Arg Thr Arg Arg Ala Arg Arg Asn Arg
1               5                   10

<210> SEQ ID NO 36
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 36

Lys Leu Thr Arg Ala Gln Arg Arg Ala Ala Arg Lys Asn Lys Arg
1               5                   10                  15

Asn Thr Arg

<210> SEQ ID NO 37
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 37

Asn Ala Lys Thr Arg Arg His Glu Arg Arg Lys Leu Ala Ile Glu
1               5                   10                  15

Arg

<210> SEQ ID NO 38
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 38

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 39
<211> LENGTH: 18
<212> TYPE: PRT
<213> ORGANISM: Artificial Sequence
<220> FEATURE:
```

<223> OTHER INFORMATION: Synthetic Sequence

<400> SEQUENCE: 39

Thr Ala Lys Thr Arg Tyr Lys Ala Arg Arg Ala Glu Leu Ile Ala Glu
1               5                   10                  15

Arg Arg

<210> SEQ ID NO 40
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 40

Thr Arg Arg Asn Lys Arg Asn Arg Ile Gln Glu Gln Leu Asn Arg Lys
1               5                   10                  15

<210> SEQ ID NO 41
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 41

Ser Gln Met Thr Arg Gln Ala Arg Arg Leu Tyr Val
1               5                   10

<210> SEQ ID NO 42
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 42

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 43
<211> LENGTH: 28
<212> TYPE: PRT
<213> ORGANISM: Artificial Sequence
<220> FEATURE:
<223> OTHER INFORMATION: Synthetic Sequence

<400> SEQUENCE: 43

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 44
<211> LENGTH: 22
<212> TYPE: PRT
<213> ORGANISM: Artificial Sequence
<220> FEATURE:
<223> OTHER INFORMATION: Synthetic Sequence

<400> SEQUENCE: 44

Lys Arg Ala Arg Asn Thr Glu Ala Ala Arg Arg Ser Arg Ala Arg Lys
1               5                   10                  15

```
Leu Gln Arg Met Lys Gln
            20

<210> SEQ ID NO 45
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 45

Lys Leu Ala Leu Lys Leu Ala Leu Lys Ala Leu Lys Ala Ala Leu Lys
1               5                   10                  15

Leu Ala

<210> SEQ ID NO 46
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 46

Leu Leu Ile Ile Leu Arg Arg Arg Ile Arg Lys Gln Ala Lys Ala His
1               5                   10                  15

Ser Lys

<210> SEQ ID NO 47
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 47

Arg Arg Arg Arg Arg Arg Arg Arg
1               5

<210> SEQ ID NO 48
<211> LENGTH: 32
<212> TYPE: PRT
<213> ORGANISM: Artificial Sequence
<220> FEATURE:
<223> OTHER INFORMATION: Synthetic

<400> SEQUENCE: 48

Pro Pro Leu Ser Gln Glu Thr Phe Ser Asp Leu Trp Lys Leu Leu Lys
1               5                   10                  15

Lys Trp Lys Met Arg Arg Asn Gln Phe Trp Val Lys Val Gln Arg Gly
            20                  25                  30

<210> SEQ ID NO 49
<211> LENGTH: 27
<212> TYPE: PRT
<213> ORGANISM: Artificial Sequence
<220> FEATURE:
<223> OTHER INFORMATION: Synthetic Sequence

<400> SEQUENCE: 49

Glu Thr Phe Ser Asp Leu Trp Lys Leu Leu Lys Lys Trp Lys Met Arg
1               5                   10                  15

Arg Asn Gln Phe Trp Val Lys Val Gln Arg Gly
            20                  25
```

<210> SEQ ID NO 50
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 50

Met Pro Phe Ser Thr Gly Lys Arg Ile Met Leu Gly Glu Lys Trp
1               5                   10                  15

Lys Met Arg Arg Asn Gln Phe Trp Val Lys Val Gln Arg Gly
            20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic Sequence

<400> SEQUENCE: 51

Thr Ile Glu Asp Ser Tyr Arg Lys Gln Val Val Ile Asp Lys Lys Trp
1               5                   10                  15

Lys Met Arg Arg Asn Gln Phe Trp Val Lys Val Gln Arg Gly
            20                  25                  30

<210> SEQ ID NO 52
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 52

Thr Ile Glu Asp Ser Tyr Arg Lys Gln Val Val Ile Asp
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 53

Gly Cys Cys Ala Cys Cys Ala Thr Gly Gly
1               5                   10

<210> SEQ ID NO 54
<211> LENGTH: 64
<212> TYPE: PRT
<213> ORGANISM: Artificial Sequence
<220> FEATURE:
<223> OTHER INFORMATION: Synthetic Sequence

<400> SEQUENCE: 54

Ala Gly Thr Cys Gly Ala Ala Thr Thr Cys Gly Cys Ala Cys Cys
1               5                   10                  15

Ala Thr Gly Gly Ala Ala Ala Cys Ala Thr Thr Thr Cys Ala Gly
            20                  25                  30

Ala Cys Cys Thr Ala Thr Gly Gly Ala Ala Ala Cys Thr Ala Cys Thr
            35                  40                  45

Thr Thr Gly Ala Gly Cys Gly Gly Cys Cys Gly Cys Ala Gly Thr Cys
    50                  55                  60

```
<210> SEQ ID NO 55
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 55

Glu Thr Phe Ser Asp Leu Trp Lys Leu Leu
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 56

Pro Pro Leu Ser Gln Glu Thr Phe Ser
1               5
```

COMPOSITIONS FOR USE IN LYSIS OF SELECTIVE CANCER CELLS

CROSS-REFERENCE TO RELATED APPLICATIONS

This application is a National Stage Application that claims a benefit of priority from Application No. PCT/US2019/026390 filed Apr. 8, 2019, which claims priority to Provisional Application No. 62/653,808, filed Apr. 6, 2018, the disclosures of which are herein incorporated in their entirety.

FIELD OF THE INVENTION

The invention relates to methods of effectively treating various forms of cancer. Specifically, the present invention is directed to methods to treat cancer by necrosis, membranolysis, or poration of selective cancer cells.

RELATED ART

Cancer treatments which target the p53-HDM2 protein interaction within cancer cells have been developed recently. However, some types of cancer cells do not have p53, while others exhibit p53 in a mutated, and/or inactive form. Thus, these p53 targeting cancer treatments are limited since they do not cause cell death in these types of cancer cells. Thus, p53-targeting cancer treatments are ineffective at treating various types of cancer.

SUMMARY OF THE INVENTION

In one aspect, the present invention provides a method of treating cancer in a subject in need thereof, comprising administering to the subject a therapeutically effective amount of a composition comprising a human double minute binding domain (HDM-2) targeting component and a membrane resident component (MRC), wherein the cancer is selected from the group consisting of: acute myeloid leukemia (AML), chronic lymphocytic leukemia (CLL), chronic myeloid leukemia (CML), Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell acute lymphoblastic leukemia (ALL), Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous.

In another aspect, the present invention provides a method of necrosing or causing membranolysis of selective cancer cells, comprising providing a plurality of cells, comprising at least one cancer cell and at least one normal cell, administering to the cells a composition comprising an HDM-2 targeting component and a membrane resident component, and wherein said peptide results in necrosis or membranolysis of said cancer cells, but does not affect said normal cells; wherein the cancer is selected from the group consisting of: AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous.

In another aspect, the present invention provides a method of necrosing or causing poration of selective cancer cells, comprising providing a plurality of cells, comprising at least one cancer cell and at least one normal cell, administering to the cells a composition comprising an HDM-2 targeting component and a membrane resident component, and wherein said composition results in necrosis or causing poration of said cancer cells, but does not affect said normal cells; wherein the cancer is selected from the group consisting of: AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous.

DETAILED DESCRIPTION

Figure 1A:
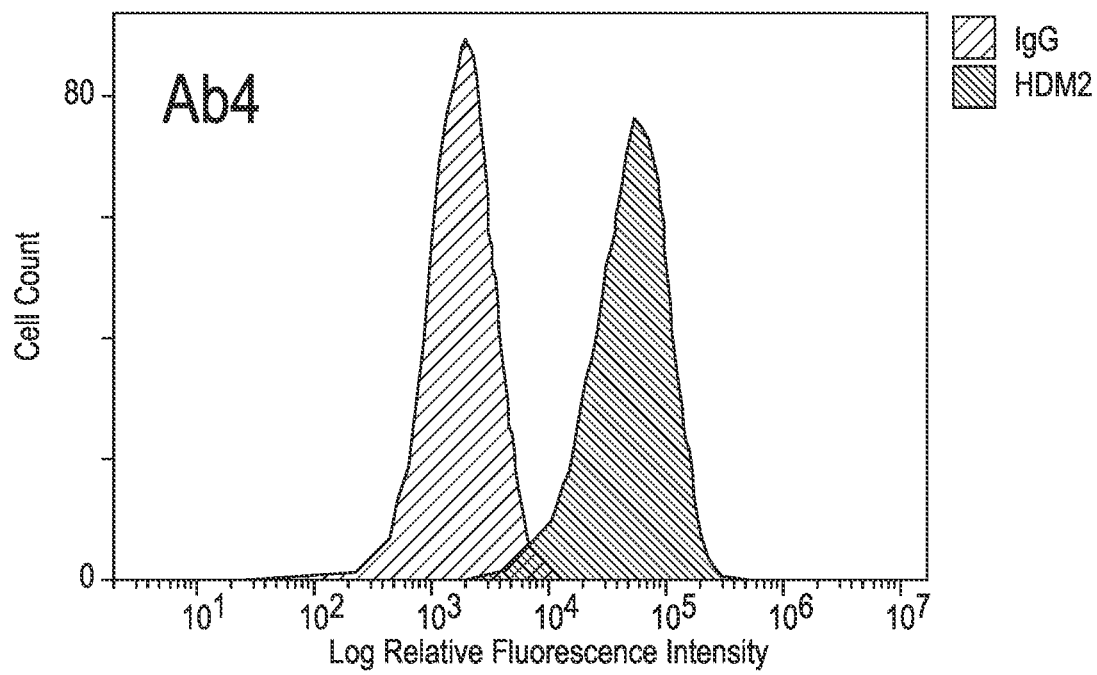
FIG. 1 depicts flow cytometry data showing HDM2 on the surface of two AML cell lines (A) OCI-AML and (B) THP-1. The separation of the two fluorescence peaks (one from an IgG control signal, on the left, and the other from an HDM2 signal) reveal the presence of HDM2 on the cell surface of acute myeloid leukemia cells.

This invention relates to the selective mechanism of action of certain compositions having an HDM-2 targeting component and a membrane resident component; that when administered to selective cancer cells and normal non-cancerous cells, necrosis of selective cancer cells occurs, but the normal non-cancerous cells are unaffected. This surprising result led to the invention of the novel methods to treat cancer, and compositions of the present invention for treating the same. More specifically, this invention involves methods of treatment and compositions of synthetic peptide, non-peptide, and combination molecules for treating cancer, where the synthetic peptide, non-peptide, and combination molecules described herein selectively destroy malignant and transformed cells only, even when administered to a mixture of normal non-cancerous cells and cancer cells.

In one embodiment, the present invention includes a method of treating a selective cancer in a subject in need thereof, comprising administering to the subject a therapeutically effective amount of a composition comprising an HDM-2 targeting component and a membrane resident component (MRC).

As used herein, the selective cancers referenced above include AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous.

In one embodiment, selective cancers include breast cancer subtypes, including Ductal Carcinoma In Situ (DCIS), Invasive Ductal Carcinoma (IDC), IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, Invasive Lobular Carcinoma (ILC), Inflammatory Breast Cancer, Lobular Carcinoma In Situ (LCIS), Male Breast Cancer, Molecular Subtypes of Breast Cancer, Paget's Disease of the Nipple, Phyllodes Tumors of the Breast, and Metastatic Breast Cancer.

Molecular subtypes of breast cancer including Luminal A breast cancer is hormone-receptor positive (estrogen-receptor and/or progesterone-receptor positive), HER2 negative, and has low levels of the protein Ki-67, which helps control how fast cancer cells grow.

Luminal B breast cancer is hormone-receptor positive (estrogen-receptor and/or progesterone-receptor positive), and either HER2 positive or HER2 negative with high levels of Ki-67.

Triple-negative/basal-like breast cancer is hormone-receptor negative (estrogen-receptor and progesterone-receptor negative) and HER2 negative. This type of cancer is more common in women with BRCA1 gene mutations.

HER2-enriched breast cancer is hormone-receptor negative (estrogen-receptor and progesterone-receptor negative) and HER2 positive.

In another embodiment, selective cancers include colon cancer subtypes, including adenocarcinoma (cancer of the cells that line the inside surface of the colon), carcinoid tumors (start in the hormone-producing cells in the intestines), gastrointestinal stromal tumors (stromal tumors found in the colon), lymphoma (originating in the colon), and hereditary colon cancer.

In another embodiment, selective cancers include ovarian cancer subtypes, including ovarian epithelial cancer, germ cell tumors, sex cord-stromal tumors, ovarian sarcoma, krukenberg tumors, ovarian cysts, and recurrent ovarian cancer. Examples of ovarian epithelial cancer include primary peritoneal carcinoma and fallopian tube cancer. Ovarian germ cell tumors include teratomas, dysgerminoma ovarian germ cell cancer, and endodermal sinus tumor. Sex cord-stromal tumors include granulosa cell tumors, granulosa-theca tumors, and sertoli-leydig tumors. Ovarian sarcoma tumors develop in the connective tissues of ovarian cells. Their most common subtypes are carcinosarcomas, adenosarcomas, leiomyosarcomas, and fibrosarcomas. A Krukenberg tumor is cancer that spreads to the ovaries from other organs, typically from the gastrointestinal tract. Ovarian cysts are fluid-filled sacs that develop inside the ovary.

In another embodiment, selective cancers include pancreatic cancer and pancreatic cancer subtypes, including exocrine tumors and endocrine tumors. Exocrine tumors include adenocarcinoma, ductal adenocarcinoma and acinar adenocarcinoma. Endocrine tumors are also called pancreatic neuroendocrine tumors (PNET) or islet cell tumors. Examples of endocrine tumors include Insulinoma, Glucagonoma, Gastrinoma, Somatostatinoma, VlPomas, and PPomas.

In another embodiment, selective cancers include melanoma and melanoma subtypes, including Superficial spreading melanoma, Nodular melanoma, Lentigo maligna melanoma, Acral lentiginous melanoma. Ocular melanoma and anorectal melanoma are also contemplated.

In another embodiment, selective cancers include cervical cancer and cervical cancer subtypes, including squamous cell carcinoma, and adenocarcinoma that develop in the glandular cells that line the upper portion of the cervix.

In another embodiment, selective cancers include melanoma and melanoma subtypes, including superficial spreading melanoma, nodular melanoma, lentigo maligna melanoma, amelanotic melanoma, desmoplastic melanoma, and acral lentiginous melanoma.

In another embodiment, selective cancers include prostate cancer and prostate cancer subtypes, including acinar adenocarcinoma, ductal adenocarcinoma, transitional cell (or urothelial) cancer, squamous cell cancer, and small cell prostate cancer.

In another embodiment, selective cancers include lung cancer and lung cancer subtypes, including small cell lung cancer (SCLC) and non-small cell lung cancer including adenocarcinoma, squamous cell lung cancer (epidermoid carcinoma), and large cell lung cancer. Other lung cancer subtypes are contemplated, and include sarcomatoid carcinoma, salivary gland tumor, and other unclassified tumors of the lung.

In another embodiment, selective cancers include skin cancer, including squamous cell skin cancer or basal cell skin cancer. In some embodiments, the skin cancer may be primary skin cancer. In some embodiments, the skin cancer may be secondary skin cancer.

In another embodiment, selective cancers include hairy cell leukemia. Hairy cell leukemia may be characterized by abnormal B cells that appear to be "hairy" under the microscope.

As used herein, the selective cancers include primary or metastatic cancers.

As used herein, the selective cancers include primary and secondary types.

As used herein, to "selective" cancers means preferential necrosis, membranolysis, or poration of one cancer cell type over another cancer cell type or normal cell type. For example, a compositions disclosed herein may cause necrosis, membranolysis, or poration more than 1 fold, such as greater than 2 fold, 3 fold, 4 fold, 5 fold, 6 fold, 7 fold, 8 fold, 9 fold, 10 fold, 20 fold, 30 fold, 40 fold, 50 fold, 100 fold, 200 fold, 300 fold, 400 fold, 500 fold, or 1000 fold, in comparison to necrosis, membranolysis, or poration of one cancer cell type over another cancer cell type or normal cell type.

As used herein, "normal cell type" means non-cancerous cell type.

HDM-2 Targeting Component

In one embodiment, the HDM-2 targeting component is a peptide that is selective for HDM-2. The peptide can be synthesized by any method known in the art. Furthermore, the peptide may include a functional group at the N-terminus or C-terminus that allows for conjugation to a small molecule or peptide. In this embodiment, the polypeptide may include alkynylene, alkoxy, azide, N-Hydroxysuccinimide Esters, imidoester, carbdiimides, maleimide, haloacetyl, pyridyl disulfide, and diazirine.

Examples of functional groups and reactions suitable for use in conjugation described above include:

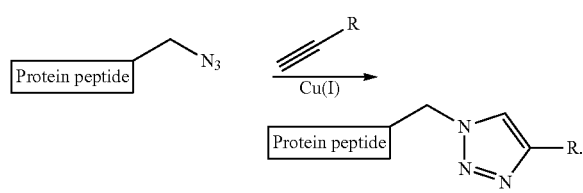

Such methods of conjugation are known in the art. For example, as described in Hermanson Bioconjugate Techniques, Third Edition (2013) (ISBN-10: 0123822394); the contents of which are incorporated herein by reference.

TABLE 1

HDM-2 Binding Peptides.

| SEQ ID NO: | HDM-2 TARGETING COMPONENT |
|---|---|
| 1 | PPLSQETFSDLWKLL |
| 2 | ETFSDLWKLL |
| 3 | MPRFMDYWEGLN |
| 4 | VQNFIDYWTQQF |
| 5 | TGPAFTHYWATF |
| 6 | IDRAPTFRDHWFALV |
| 7 | PRPALVFADYWETLY |
| 8 | PAFSRFWSDLSAGAH |
| 9 | PXFXDYWXXL |
| 10 | QPTFSDYWKLLP |
| 11 | PPL--TSFXEYWALLX-P |
| 12 | PPLSQTSFAEYWNLL |
| 13 | LTFEHYWAQLTS |
| 14 | TSFAEYWNLLSP |
| 15 | QETFSDLWKLLP |
| 16 | MPRFMDYWEGLN |
| 17 | QQMHLMSYAPGP |
| 18 | TIRPSTTMDSPT |
| 19 | YANPQMEKAFES |
| 20 | LTFEHYWAQLTS |
| 21 | LPNLTWALMPGA |
| 22 | YANPQMEKAFAS |
| 23 | LTFEHYWAQLTS |
| 24 | LLADTTHHRPWT |

In one embodiment, the HDM-2 targeting component is an antibody or antibody fragment. In one embodiment, the HDM-2 targeting component is an antibody that is selective for HDM-2. In one embodiment, the antibody fragment is an antibody fragment that is selective for HDM-2 For example, the antibody fragment includes scFv, sdAb, di-scFv. sdAb is a single domain antibody. scFv includes the VH and VL domains of an antibody and is connected by a linker. di-scFv includes two scFv molecules connect by a linker.

The antibody may be a monoclonal antibody or polyclonal antibody. In one embodiment, the antibody is selective for the surface exposed portions of HDM-2. In one embodiment, the antibody is selective for the p53 binding site of HDM-2. In one embodiment, the antibody is selective for residues 1-109 of HDM-2; 1-50 of HDM-2; 25-75 of HDM-2; or 50-109 of HDM-2.

In another embodiment, the antibody is a Camelid single domain antibody, or portions thereof. In one embodiment, Camelid single-domain antibodies include heavy-chain antibodies found in camelids, or VHH antibody. A VHH antibody of camelid (for example camel, dromedary, llama, and alpaca) refers to a variable fragment of a camelid single-chain antibody (See Nguyen et al, 2001; Muyldermans, 2001), and also includes an isolated VHH antibody of camelid, a recombinant VHH antibody of camelid, or a synthetic VHH antibody of camelid.

As used herein, antibody includes antibody fragments.

In another embodiment, the HDM-2 targeting component is a small molecule.

In one embodiment, the HDM-2 binding component is

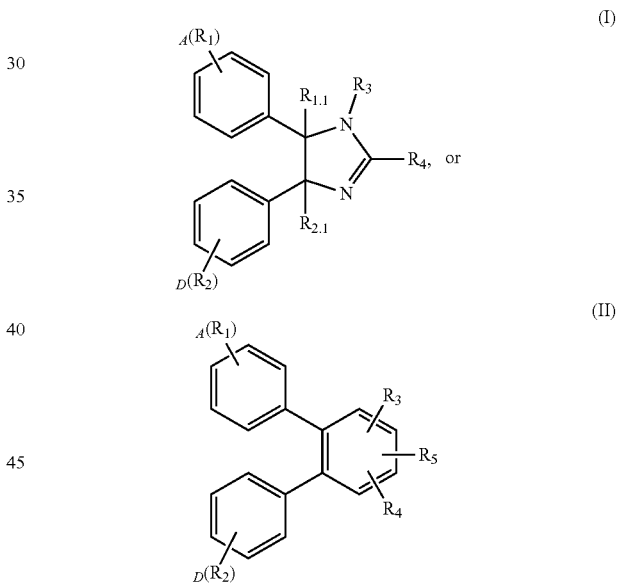

wherein R1, R1.1, R2, and R2.1 are independently H, halogen, lower alkylene, lower alkenylene, or lower alkynylene, optionally, with the proviso that when R1 or R2 is in the para position, R1 or R2 is not Br;

R3, R4, and R5 are independently H, halogen, lower alkylene, lower alkenylene, lower alkynylene, alkoxy, azide, N-Hydroxysuccinimide Esters, imidoester, carbdiimides, maleimide, haloacetyl, pyridyl disulfide, or diazirine,

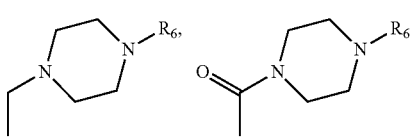

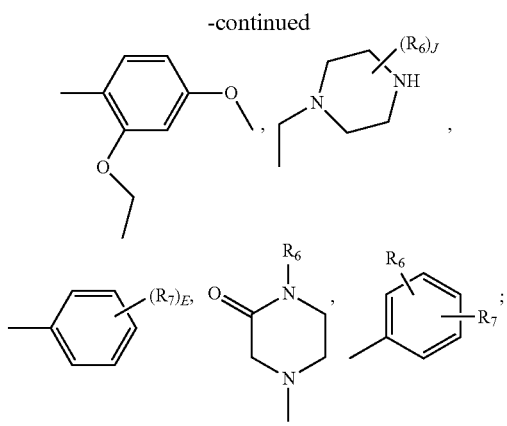

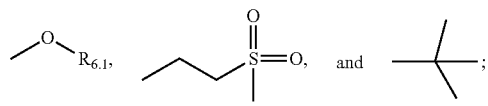

wherein R6 and R7 are independently H, halogen, lower alkylene, lower alkenylene, lower alkynylene, alkoxy, or R6.1 is H, halogen, lower alkylene, lower alkenylene, lower alkynylene; A, D, E, G, and J are independently 1, 2, 3, 4, or 5.

In one embodiment, $R_3$, $R_4$, $R_5$, $R_6$, or $R_7$ includes a functional group which allows conjugation to the membrane resident component. Such functional groups are known in the art. For example, the functional groups include alkynylene, alkoxy, azide, N-Hydroxysuccinimide Esters, imidoester, carbdiimides, maleimide, haloacetyl, pyridyl disulfide, and diazirine. In one embodiment, R6 is $C_2H_5O$.

In one embodiment, $R_3$, $R_4$, $R_5$, $R_6$, or $R_7$ is linked or conjugated to a MRC described herein.

The above molecule may be synthesized by any method known in the art. See, for example. Vassilev et al., Science, 2004 Feb. 6; 303(5659):844-8; and Zhao et al., BioDiscovery 2013.

In one embodiment, the above molecule may be conjugated to the N-terminus, C-terminus, lysine, cysteine, or tyrosine of membrane resident component polypeptide. In this embodiment, a membrane resident component polypeptide may include additional lysine, cysteine, or tyrosine residues at the N-terminus, C-terminus, or added to any of the polypeptides disclosed herein.

Examples of small molecule HDM-2 targeting components include

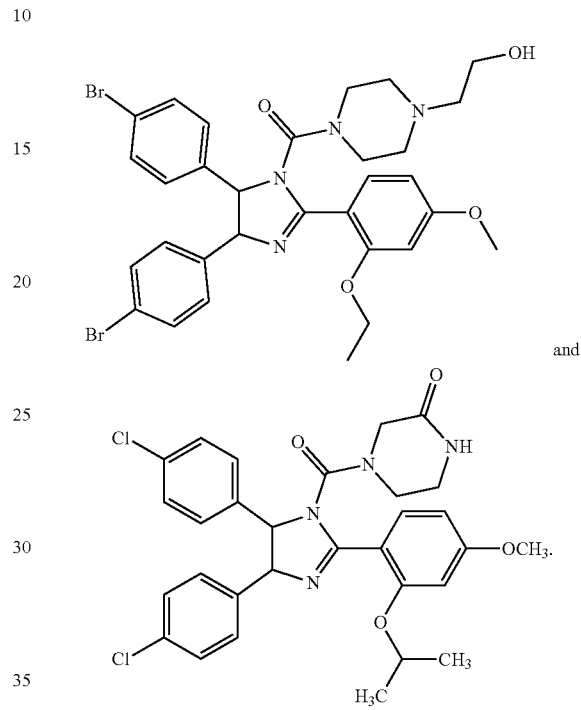

and

Membrane Resident Component

In one embodiment, the membrane resident component (MRC) is a peptide or a membrane resident peptide (MRP). In one embodiment, the MRP may include a functional group that allows conjugation to a small molecule HDM-2 targeting component, as described above.

TABLE 2

Membrane Resident Peptides (MRP).

| SEQ ID NO: | NAME | MRP |
|---|---|---|
| 25 | Membrane resident peptide (MRP), reverseomer of Antennapedia | KKWKMRRNQFWVKVQRG |
| 26 | peptide from cytochrome P450 (aka "X13") | MPFSTGKRIMLGE |
| 27 | HIV-1 TAT(47-60), membrane resident peptide | YGRKKRRQRRRPPQ |
| 28 | D-TAT, membrane resident peptide | GRKKRRQRRRPPQ |
| 29 | R-TAT G(R)₉PPQ, membrane resident peptide | GAAAAAAAAAPPQ |
| 30 | SV40-NLS, membrane resident peptide | PKKKRKV |

TABLE 2 -continued

Membrane Resident Peptides (MRP).

| SEQ ID NO: | NAME | MRP |
|---|---|---|
| 31 | nucleoplasmin-NLS, membrane resident peptide | KRPAAIKKAGQAKKKK |
| 32 | HIV REV (34-50), membrane resident peptide | TRQARRNRRRRWRERQR |
| 33 | FHV (35-49) coat, membrane resident peptide | RRRRNRTRRNRRRVR |
| 34 | BMV GAG (7-25), membrane resident peptide | KMTRAQRRAAARRNRWTAR |
| 35 | HTLV-II REX 4-16, membrane resident peptide | TRRQRTRRARRNR |
| 36 | CCMV GAG (7-25), membrane resident peptide | KLTRAQRRAAARKNKRNTR |
| 37 | P22 N (14-30), membrane resident peptide | NAKTRRHERRRKLAIER |
| 38 | LAMBDA N(1-22), membrane resident peptide | MDAQTRRRERRAEKQAQWKAAN |
| 39 | Phi N (12-29), membrane resident peptide | TAKTRYKARRAELIAERR |
| 40 | YEAST PRP6 (129-124), membrane resident peptide | TRRNKRNRIQEQLNRK |
| 41 | HUMAN U2AF, membrane resident peptide | SQMTRQARRLYV |
| 42 | HUMAN C-FOS (139-164), membrane resident peptide | KRRIRRERNKMAAAKSRNRRRELTDT |
| 43 | HUMAN C-JUN (252-279), membrane resident peptide | RIKAERKRMRNRIAASKSRKRKLERIAR |
| 44 | YEAST GCN4, membrane resident peptide | KRARNTEAARRSRARKLQRMKQ |
| 45 | Example membrane resident peptide (MRP) | KLALKLALKALKAALKLA |
| 46 | p-vec, membrane resident peptide | LLIILRRRIRKQAKAHSK |
| 47 | (Arg)$_8$ or any poly-R from (R)$_4$-(R)$_{16}$, membrane resident peptide | RRRRRRRR |

In one embodiment, the MRC is a small molecule. For example, the MRC is

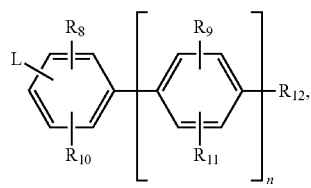

wherein L is linked or conjugated to a HDM-2 targeting component; n is 0, 1, 2, 3, 4, 5, 6, 7; in one embodiment, n is an even number between 0 and 100.

L may be a functional group which allows conjugation to a similarly functionalized molecule or capable of reacting with L, when L is: $(Z)_m NR_{15}R_{16}$ where Z is a hydrocarbyl group and m is 0 or 1; where $R_{15}$ and $R_{16}$ are each independently H, $CO(CH_2)_j Q_1$ or $C=S(NH)(CH_2)_k Q_2$ where j and k are each independently 0, 1, 2, 3, 4, or 5, and $Q_1$ and $Q_2$ are each independently selected from COOH, a chromophore

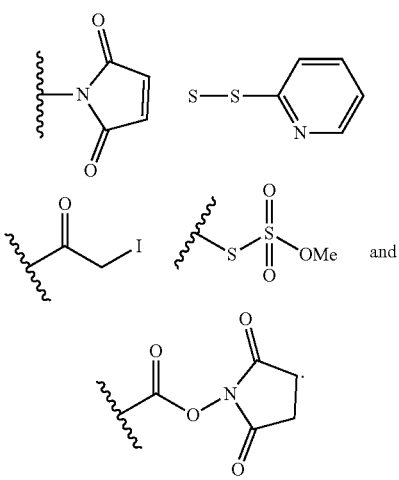

$R_8$, $R_9$, $R_{10}$, and $R_{11}$ are each independently

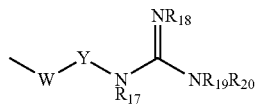

where Y is an alkylene, alkenylene, or alkynylene group, each of which may be optionally substituted with one or more substituents selected from alkyl, halo, $CF_3$, OH, alkoxy, $NH_2$, CN, $NO_2$, and COOH; W is absent or is O, S, or NH; $R_{17}$, $R_{18}$, $R_{18}$, and $R_{20}$ are each independently selected from H, alkyl, aryl, and a protecting group P1. Protecting groups are commonly known in the art. An example of a suitable protecting group includes tert-Butyloxycarbonyl (BOC).

In one embodiment, $R_8$, $R_9$, $R_{10}$, and $R_{11}$ are each $R_{12}$ is 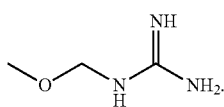

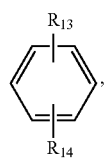

wherein
$R_{13}$ and $R_{14}$ are each independently

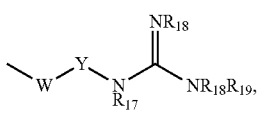

where Y is an alkylene, alkenylene, or alkynylene group, each of which may be optionally substituted with one or more substituents selected from alkyl, halo, $CF_3$, OH, alkoxy, $NH_2$, CN, $NO_2$, and COOH; W is absent or is O, S, or NH; $R_{17}$, $R_{18}$, $R_{19}$, and $R_{20}$ are each independently selected from H, alkyl, aryl, and a protecting group P1.

The above molecule may be synthesized by any method known in the art. See, for example, Okuyama et al., Nature Methods, January 2007.

In another embodiment, the membrane resident component includes a polypeptide configured to conjugate to the compound of formula I or formula II. In this embodiment, the polypeptide may include alkynylene, alkoxy, azide, N-Hydroxysuccinimide Esters, imidoester, carbdiimides, maleimide, haloacetyl, pyridyl disulfide, and diazirine.

HDM-2 and MRC

The HDM-2 targeting component and MRC as described above are covalently linked. They may be linked directly or by way of a linker. Compositions having a HDM-2 targeting component that are conjugated or covalently linked to a MRC or MRP define the compositions disclosed herein.

The peptides of the present invention include a HDM-2 targeting component and a membrane resident component (MRP). In the case of the HDM-2 targeting component is a polypeptide, it may be conjugated to the N-terminus or the C-terminus of the MRP.

The peptides of the present invention may include, for example, PNC-27 and PNC-28. The HDM-2 targeting components may be, for example, the residues of p53 which bind to HDM-2. Both PNC-27 and PNC-28 are examples of p53-derived peptides from the human double minute binding domain (HDM-2) that are attached to MRP. These peptides induce tumor cell necrosis of cancer cells, but not normal cells. The anti-cancer activity and mechanism of PNC-28 (p53 aa17-26-MRP) was specifically studied against human pancreatic cancer, though uses and applications are included with the various methods of the present invention.

The MRC is necessary for this action since expression of the naked p53 sequence without MRC in cancer cells causes wild-type p53-dependent apoptosis, or programmed cell death, not tumor cell necrosis.

In one embodiment, the MRC is an MRP. Preferably, the MRP includes predominantly positively charged amino acid residues since a positively charged leader sequence, which may stabilize the alpha helix of a subject peptide. Examples of MRPs which may be useful to the HDM-2 targeting components of the present invention are described in Futaki, S. et al (2001) Arginine-Rich Peptides, J. Biol. Chem. 276:5836-5840, and include but are not limited to the MRPs listed in TABLE 2. The MRP may be, for example, peptides included in SEQ ID NO: 25-47. The numbering of the amino acid residues making up the MRP is indicated before the name of the component in most of the examples in most of the sequence listings, and in Table 2.

In one embodiment, the polypeptide HDM-2 targeting component and the MRP may be independently stabilized.

TABLE 3

| SEQ ID: | Name | Sequence |
|---|---|---|
| 48 | PNC-27 | PPLSQETFSDLWKLL KKWKMRRNQFWVKVQRG |
| 49 | PNC-28 | ETFSDLWKLLKKWKMRRNQFWVKVQRG |
| 50 | PNC-29 | MPFSTGKRIMLGEKKWKMRRNQFWVKVQRG |
| 51 | PNC-7 | TIEDSYRKQVVIDKKWKMRRNQFWVKVQRG |

TABLE 3 -continued

| SEQ ID: | Name | Sequence |
|---|---|---|
| 52 | ras-p21 residues 35-47 | TIEDSYRKQVVID |
| 53 | Kozak sequence | GCCACCATGG |
| 54 | sense strand sequence of cDNA encoding the p53 17-26 sequence | AGTCGAATTCGCCACCATGGAAACATT TTCAGACCTATGGAAACTACTTTGAGCGGC CGCAGTC |
| 55 | residues 17-26 of HDM-2 binding domain of p53 | ETFSDLWKLL |
| 56 | PNC-21 | PPLSQETFS |

In one embodiment, the HDM-2 targeting component and the MRC are small molecules. For example, the following structure is an example of a small molecule HDM-2 targeting component bound to an MRC.

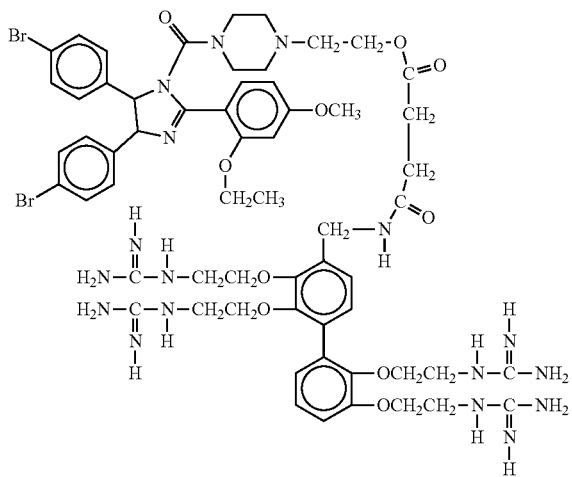

In another embodiment, the HDM-2 targeting component is an antibody, as described above, and the MRC is a peptide (MRP). The C-terminus or the N-terminus of the MRP may be conjugated to the HDM-2 targeting antibody.

In another embodiment, the HDM-2 targeting component is an antibody, as described above, and the MRC is a small molecule.

In another embodiment, the HDM-2 targeting component is a peptide and the MRC is a small molecule.

In another embodiment, the HDM-2 targeting component is a small molecule and the MRC is a peptide (MRP).

The HDM-2 targeting component and the MRC may be attached by way of a linker. The linker may be a peptide linker, macromolecular linker, chemical linker, or polymeric linker.

Peptide linker may have a maximum length of 6, 7, 8, 9, 10, 11, 12, 13, 14, 15, 20, 25, 50, or 100 amino acid residues. The peptide linker may have a minimum of 1, 2, 3, 4, 5, 6, 7, 8, 9, 10, 25, or 50 amino acid residues.

In one embodiment, the linker is polyglutamic acid (PGA).

Examples of other suitable linkers include polyethylene glycol (PEG). The PEG may be branched or linear and each PEG may have a molecular weight between about 200 and 100,000 Daltons. In one embodiment, the PEG has a minimum molecular weight of 400, 500, 1,000, 2,500, 5,000, or 10,000. In one embodiment, the PEG has a maximum molecular weight of 1,000, 2,500, 5,000, 10,000, 25,000, 50,000, 75,000, or 100,000.

In one embodiment, the PEG includes multi-arm PEG.

In one embodiment, the linker is polysarcosine (PSR) polyoxazolines, polyactides, poly lactide-co-glycolide (PLGA), or chitosan.

The linker may be the result of a conjugation reaction between the functional group on the HDM-2 targeting component and the MRC.

The synthetic peptides of the present invention may be synthesized by a number of known techniques. For example, the peptides may be prepared using the solid-phase technique initially described by Merrifield (1963) in J. Am. Chem. Soc. 85:2149-2154. Other peptide synthesis techniques may be found in M. Bodanszky et al. Peptide Synthesis, John Wiley and Sons, 2d Ed., (1976) and other references readily available to those skilled in the art. A summary of polypeptide synthesis techniques may be found in J. Stuart and J. S. Young, Solid Phase Peptide Synthesis, Pierce Chemical Company, Rockford, Ill., (1984). Peptides may also be synthesized by solid phase or solution methods as described in The Proteins, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, Protective Groups in Organic Chemistry, Plenum Press, New York, N.Y. (1973). The peptides of the present invention may also be prepared by chemical or enzymatic cleavage from larger portions of the p53 protein or from the full length p53 protein. Likewise, membrane-resident sequences for use in the synthetic peptides of the present invention may be prepared by chemical or enzymatic cleavage from larger portions or the full length proteins from which such leader sequences are derived.

The synthetic small molecules of the present invention may be synthesized by a number of known techniques. For example, a molecule according to the present invention may be synthesized as follows.

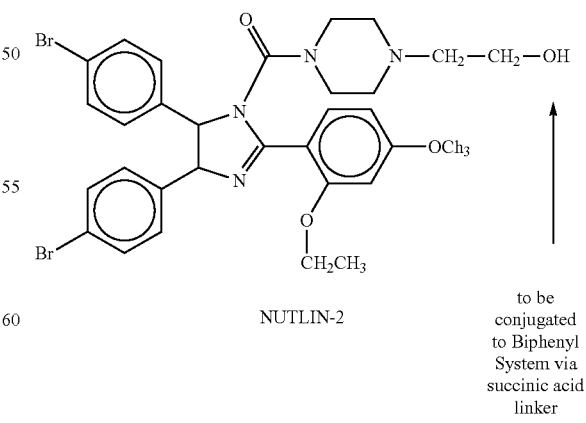

NUTLIN-2 to be conjugated to Biphenyl System via succinic acid linker

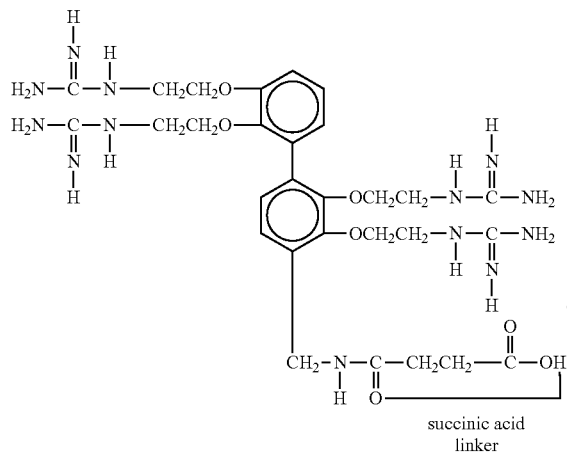

succinic acid linker

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide selectively lethal to malignant and transformed mammalian cells. The present invention also contemplates a deoxyribonucleic acid (DNA) molecule that defines a gene coding for, i.e., capable of expressing a subject peptide or a chimeric peptide from which a peptide of the present invention may be enzymatically or chemically cleaved.

Methods of Treatment

In one embodiment, the compositions disclosed herein necrose, cause poration, or cause membranolysis of selective cancer cells and do not cause necrosis or membranolysis of other cancer cells. In one embodiment, the compositions disclosed herein disclosed herein selectively necrose the following cancer cells: AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous.

The terms "therapeutically effective dosage" and "effective amount" refer to an amount sufficient to kill one or more cancer cells. A therapeutic response may be any response that a user (e.g. a clinician will recognize) exhibits as an effective response to the therapy, including the foregoing symptoms and surrogate clinical markers. Thus, a therapeutic response will generally be an amelioration or inhibition of one or more symptoms of a disease or disorder, e.g. cancer.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight. In an exemplary embodiment, one or more doses of 10 to 150 mg/day will be administered to the patient.

The term subject, as used herein may refer to a patient or patient population diagnosed with, or at risk of developing one or more forms of cancer described herein. A subject includes mammals, including humans. They may also include household pets or other animals in need of treatments for a cancer described herein. Also, as used herein, a subject may refer to a living animal, including mammals, which may be given cancer through transplantation or xenotransplanting which may be subsequently treated with the methods and compositions of the present invention or which have developed a cancer described herein and need veterinary treatment. Such subjects may include mammals, for example, laboratory animals, such as mice, rats, and other rodents; cats and dogs; and monkeys, baboons, and other primates.

Further to the methods described herein, the administration step may be done through various forms, as is known. Administration of the compositions of the present invention may be by oral, intravenous, intra-arterial, intranasal, suppository, intraperitoneal, intramuscular, intradermal or subcutaneous administration or by infusion or implantation into the body, including direct injection or placement inside a tumor. When administered in such manner, the compositions of the present invention may be combined with other ingredients, such as carriers and/or adjuvants. There are no limitations on the nature of the other ingredients, except that they are preferably pharmaceutically acceptable, efficacious for their intended administration, preferably do not degrade the activity of the active ingredients of the compositions, and preferably do not impede importation of a subject composition into a cell. The compositions disclosed herein may also be impregnated into transdermal patches, or contained in subcutaneous inserts, preferably in a liquid or semi-liquid form which patch or insert time-releases therapeutically effective amounts of one or more of the subject synthetic peptides or compositions disclosed herein.

The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents.

Administering may include contacting. The term "contacting" refers to directly or indirectly bringing the cell and the compositions disclosed herein together in physical proximity. The contacting may be performed in vitro or in vivo. For example, the cell may be contacted with the composition by delivering the compositions disclosed herein into the cell through known techniques, such as microinjection into the tumor directly, injecting the compositions disclosed herein into the bloodstream of a subject, and incubating the cell in a medium that includes the compositions disclosed herein.

The compositions of the invention are administered to a human in an amount effective in achieving its purpose. The effective amount of the composition to be administered can be readily determined by those skilled in the art, for example, during pre-clinical trials and clinical trials, by methods familiar to physicians and clinicians. Typical daily doses include approximately 1 mg to 1000 mg.

Any method known to those in the art for contacting a cell, organ or tissue with a pharmaceutical composition may be employed. Suitable methods include in vitro, ex vivo, or in vivo methods. In vitro methods typically include cultured samples. For example, a cell can be placed in a reservoir (e.g., tissue culture dish), and incubated with a composition disclosed herein under appropriate conditions suitable for inducing necrosis in cancer cells. Suitable incubation conditions can be readily determined by those skilled in the art.

Ex vivo methods typically include cells, organs or tissues removed from a mammal, such as a human. The cells, organs or tissues can, for example, be incubated with the compositions disclosed herein under appropriate conditions. The contacted cells, organs or tissues are normally returned to the donor, placed in a recipient, or stored for future use. Thus, the composition is generally in a pharmaceutically acceptable carrier.

In vivo methods are typically limited to the administration of a composition disclosed herein, such as those described above, to a mammal, preferably a human. The compositions disclosed herein useful in the methods of the present invention are administered to a mammal in an amount effective in necrosing cancer cells for treating cancer in a mammal. The effective amount is determined during pre-clinical trials and clinical trials by methods familiar to physicians and clinicians.

An effective amount of the composition disclosed herein useful in the methods of the present invention, preferably in a pharmaceutical composition, may be administered to a mammal in need thereof by any of a number of well-known methods for administering pharmaceutical compositions. The compositions disclosed herein may be administered systemically or locally.

The compositions useful in the methods of the invention may also be administered to mammals by sustained release, as is known in the art. Sustained release administration is a method of drug delivery to achieve a certain level of the drug over a particular period of time. The level typically is measured by serum or plasma concentration.

Any formulation known in the art of pharmacy is suitable for administration of the compositions useful in the methods of the present invention. For oral administration, liquid or solid formulations may be used. Some examples of formulations include tablets, capsules, such as gelatin capsules, pills, troches, elixirs, suspensions, syrups, wafers, chewing gum and the like. The compositions disclosed herein can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums, and glycols.

Formulations of the compositions useful in the methods of the present inventions may utilize conventional diluents, carriers, or excipients, such as those known in the art to deliver the compositions. For example, the formulations may comprise one or more of the following: a stabilizer, a surfactant, preferably a nonionic surfactant, and optionally a salt and/or a buffering agent. The compositions may be delivered in the form of an aqueous solution, or in a lyophilized form. Similarly, salts or buffering agents may be used with the compositions disclosed herein.

The compositions of the present invention may be administered in therapeutically effective concentrations, to be provided to a subject in standard formulations, and may include any pharmaceutically acceptable additives, such as excipients, lubricants, diluents, flavorants, colorants, buffers, and disintegrants. Standard formulations are well known in the art. See, e.g. Remington's pharmaceutical Sciences, 20th edition, Mach Publishing Company, 2000. The formulation may be produced in useful dosage units for administration by any route that will permit the compositions to contact the cancer cell membranes. Exemplary routes of administration include oral, parenteral, transmucosal, intranasal, insulfation, or transdermal routes. Parenteral routes include intravenous, intra-arterial, intramuscular, intradermal, subcutaneous, intraperitoneal, intraductal, intraventricular, intrathecal, intratumoral, and intracranial administrations.

The compositions of the present invention may be administered as a solid or liquid oral dosage form, e.g. tablet, capsule, or liquid preparation. The compositions may also be administered by injection, as a bolus injection or as a continuous infusion. The compositions may also be administered as a depot preparation, as by implantation or by intramuscular injection.

The compositions and methods of the present invention may be admixed or otherwise combined with a pharmaceutically acceptable carrier. As used herein, a "pharmaceutically acceptable carrier" includes any and all solvents, dispersion media, coatings, antibacterial and antifungal agents, isotonic agents and the like. The use of such media and agents are well-known in the art.

The term 'pharmaceutically acceptable' refers to molecular entities and compositions that are physiologically tolerable and do not typically produce unwanted reactions when administered to a subject, particularly humans. Preferably, as used herein, the term "pharmaceutically acceptable" means approved by a regulatory agency of the federal or a state government or listed in the U.S. Pharmacopeia or other generally recognized pharmacopeia for use in animals, and more particularly, in humans. The term carrier refers to a diluent, adjuvant, excipient or vehicle with which the compositions may be administered to facilitate delivery. Such pharmaceutical carriers can be sterile liquids, such as water and oils, or organic compositions. Water or aqueous solution saline solutions, and aqueous dextrose and glycerol solutions are preferably employed as carriers, particularly as injectable solutions.

When applied to cells grown in culture, the compositions described herein are selectively lethal to malignant or transformed cells, resulting in a dose-dependent reduction in the cell number. The effect is observable generally within one, two, three, four, or five hours, and at most 48 hours or 72 hours.

One or more of the methods of the present invention may further include the step of determining whether a compositions disclosed herein reduces cancer cells activity further includes measuring the level of lactate dehydrogenase (LDH) in the cell medium, observing the cells for pore formation or membranolysis, or observing the cells breaking down over a period of time. The level of necrosis may be measured by any method known in the art, including for example, PCR analysis, RT-PCR, Northern blot, Western blot, immunohistochemistry, ELISA assays, and luciferase reporter assays.

In another embodiment, the methods of the present invention may further include the step of determining whether the compositions of the present invention causes necrosis, causes membranolysis, or causes poration of cancer cells by measuring the level of cancer by diagnostic imaging, including MRI, PET scan, and X-Ray.

In another embodiment, the methods of the present invention may further include the step of determining whether the compositions of the present invention causes necrosis, causes membranolysis, or causes poration of cancer cells by measuring the level of diagnostic cancer biomarkers before and after administration of the compositions disclosed herein.

In another embodiment, the methods of the present invention may further include the step of determining whether the compositions of the present invention causes necrosis, causes membranolysis, or causes poration of cancer cells by measuring the level of serum biomarkers. In one embodiment, the serum biomarker is LDH, cytokeratin, or HDM-2. The level of serum biomarker is measured pre- and post administration of the compositions disclosed herein. An increase in the serum biomarker between pre- and post-treatment is indicative of cancer cell necrosis, membranolysis, or poration. In one embodiment, the increase is more than 2 times greater, more than 3 times greater, or more than 5 times greater.

One or more of the methods of the present invention may be repeated or reiterated on a subject. This may be desirable, for example, if a subject suffers from refractory or relapsed cancer. Also, repeated administration may be desirable if lower dosages are administered repeatedly, over a treatment cycle or pursuant to combination therapy.

The compositions and methods of the present invention may be designed to have one or more desirable characteristics. The desirable characteristics may result in an increased effectiveness when the composition is administered to at least one cancer cell or in vivo to an organism, particularly a mammal, in need of cancer treatment.

Desirably, peptides and compositions of the present invention may have a three dimensional shape or conformation in an alpha-helix-loop-alpha-helix. This is the three-dimensional shape that has been determined for the PNC-27 and PNC-28 peptide-based compositions. The alpha-helix-loop-helix conformation allows the composition to advantageously interact with the cancer cell membrane.

It may also be desirable for the compositions of the present invention to be of a higher degree of rigidity than the synthetic peptides PNC-27 and PNC-28. As is known, peptide-based compositions have natural movement associated with their molecules. As discussed, the alpha-helix-loop-alpha-helix, that results in an amphipathic structure, in which hydrophobic amino acid residues occupy one face of the molecule while polar residues occupy the opposite face of the molecule, is a desired conformation of the molecule. A number of membrane-active peptides, such as melittin and magainin, have these required structures that result in cell membrane lysis though not with the same specificity as PNC-27. Thus, if agents can be administered to a peptide-based composition to increase the rigidity, or if a non-peptide, called a peptidomimetic, rigid molecules of similar size, with a similar amphipathic structure, may be employed with the present invention, then the conformation will more immediately affect the cancer cells. Rosal R, Brandt-Rauf P W, Pincus M R, Wang H, Mao Y, Fine R L. The role of alpha-helical structure in p53 peptides as a determinant for their mechanism of cell death: necrosis versus apoptosis. Adv Drug Deliv Rev 2005; 57:653-60; Pincus, M. R. (2001) "The Physiological Structure and Function of Proteins" in Principles of Cell Physiology (Chapter 2), Third Edition, Ed., N. Sperelakis, Academic Press, New York, pp. 19-42; 3. Dathe, M. and Wieprecht, T. (1999) Structural Features of Helical Anti-Microbial Peptides: Their Potential to Modulate Activity on Model Membranes and Biological Cells. Biochem. Biochem. Biophys. Acta 1462, 71-87.

Another desirable characteristic is for a relatively small-sized composition to be employed with the methods and as the compositions of the present invention. Large peptide, non-peptide, and combination large peptide/non-peptide compositions have the disadvantage of triggering an immunologic response with a greater likelihood than small molecules, which may go unnoticed in vivo. Thus, the immune system of the organism being treated is less likely to trigger an immune response against small molecules, i.e. peptides of <35AA than large molecule compositions, i.e., proteins with >35AA. Preferably, the synthetic peptide materials of the present invention are on the order of about fifty (50) amino acids or fewer.

Generally, as molecules (proteins) exceed 5000 D (~>35AA in size, they become immunogenic, i.e., they can elicit an immune response in the recipient. Peptides up to 5000 D (<35 AA) have been found to elicit no or only a minor immune response in the recipient. However, long-term (many months) application of peptides from 2500 D to 5000 D can result in stimulating an immune response (they can become immunogenic) in some recipients. Considering the size of the peptides disclosed herein and of the long-life constructs described below, they are all in the non- to borderline-immunogenic range. Taking into account (1) that all PNC-peptides, including those with leupeptin attached, will have a rather short lifespan (estimates are 10 to 30 min) due to removal by peptidase degradation, and (2) that they are applied to tumor-bearing patients most of which are immunologically suppressed, the likelihood of developing immunological responses that will restrict their use is very remote.

Yet another desirable characteristic for the peptide is to have a long half-life. A composition with a long half-life is able to stay in the body for longer periods of time before decomposing. Thus, a composition with a longer half-life may have an increased longevity, allowing it to be transported through the body to kill more cancer cells or treat cancers located in different parts of the organism upon a single administration. Peptide-based peptides, including PNC-27 and PNC-28, may be altered to include a D-amino acid on the amino terminal end in order to slow peptidase activity of the molecule. Similarly, leupeptin, a known peptidase activity inhibitor, may be attached to the carboxyl terminal end of PNC-27 and PNC-28 in order to slow peptidase activity and lengthen the half-life of the molecules. Moreover, additional amino acid residues can be added to the peptides disclosed herein to further aid in slowing peptidase activity and prolonging in-vivo half life. In one example, 1-9 amino acid residues can be added to the N- or C-terminus to increase half life. In one embodiment, the N- or C-terminus amino acids are selected from the group consisting of valine, methionine, glycine, proline, isoleucine, or peptidase inhibiting derivatives of amino acids. In one embodiment, an arginal is added to one or both of the N- or C-terminus.

The synthetic peptides employed with the methods of the present invention are probably likely to have half-lives on the order of minutes in situ, as is the case for most therapeutic peptides.

Throughout this specification, quantities are defined by ranges, and by lower and upper boundaries of ranges. Each lower boundary can be combined with each upper boundary to define a range. The lower and upper boundaries should each be taken as a separate element.

All patents and publications mentioned in the specification are indicative of the levels of skill of those skilled in the art to which the invention pertains. All references cited in this disclosure are incorporated by reference.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations that are not specifically disclosed herein. Thus, for example, in each instance herein any of the terms "comprising", "consisting essentially of", and "consisting" of may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventor for carrying out the invention. Variations of those embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The present invention is described by reference to the following examples, which are offered by way of illustration and are not intended to limit the invention in any manner. Standard techniques well known in the art or the techniques specifically described below are utilized.

EXAMPLES

Example 1

Cytotoxicity of PNC-27 and PNC-28 for Cancer Cells

PNC-27 or PNC-28 is incubated with $6 \times 10^6$ cancer cells, for example, Mia-PaCa-2 cells, for 5 days at concentrations ranging from 0.001-750 μM. At different timepoints following treatment the cells are assessed for signs of necrosis, for example, membrane blebbing and disruption and formation of cell clumps coalescing into aggregates of cellular debris. Percent cell death is determined by measuring trypan blue dye uptake. Cancer cells are also treated with the negative control peptide PNC-29 and, separately, a peptide having only the p53 derived portion of PNC-27 or PNC-28 that cannot traverse the cell membrane due to the lack of the MRP peptide, administered at the same concentration as the test peptide. The effect of these control peptides on cellular growth, morphology and viability is determined.

As an additional control, PNC-27 or PNC-28 is combined with untransformed BMRPA1 acinar cells and with the untransformed breast epithelial cell line, MCF-10-2A at a concentration ranging from 0.001-750 μM to determine if the peptide is lethal to normal cell growth.

Cell lines for the following cancer cells are tested AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous. Cells lines for specific subtypes of the above-identified cancers are also contemplated. Cell lines for the aforementioned cancers are well known by those of ordinary skill in the art. For Example, Ca127 is a well known cell line for Head and Neck cancers; OE33 is a well known cell line for Esophageal cancers; SKNAS is a well known cell line for Neuroblastoma; HEPG2 is a well known cell line for Liver cancers; UT7, THP-1, and OCI-AML are well known cell lines for AML; and A172 is a well known cell line for Glioblastoma.

Example 2

FACS Analysis to Determine Extracellular Expression of HDM2 on the Surface of the Cell Cells are incubated with no antibody, normal rabbit IgG (isotype control, Santa Cruz Biotechnology, Inc. item# sc-3888) or rabbit polyclonal anti-MDM2/HDM2 (clone N-20, Santa Cruz Biotechnology, Inc. item# sc-813) for 15 minutes in the dark at 4° C. Cells are then washed with 2.0 mL PBS, supernatant aspirated and 150 µL of PBS added to each tube. All cells are then incubated with a secondary goat anti-rabbit IgG conjugated to Phycoerythrin (Santa Cruz Biotechnology, Inc. item# sc-3739) for 15 minutes in the dark at 4° C. Cells are washed with 2.0 mL PBS, supernatant aspirated and 350 µL of PBS added to each tube. Samples are immediately analyzed on a BD FACSCalibur® 4-color flow cytometer using BD CellQuest Pro® software for data acquisition and analysis.

The following conditions are tested for each cell line: 2° Goat anti-Rabbit IgG PE, Rabbit normal IgG with 2° Goat anti-Rabbit IgG PE, and Anti MDM2/HDM2 with 2° Goat anti-Rabbit IgG PE.

Cell lines for the following cancer cells are tested AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous. Cell lines for the aforementioned cancers are well known by those of ordinary skill in the art. For Example, Cal27 is a well known cell line for Head and Neck cancers; OE33 is a well known cell line for Esophageal cancers; SKNAS is a well known cell line for Neuroblastoma; HEPG2 is a well known cell line for Liver cancers; UT7, THP-1, and OCI-AML are well known cell lines for AML; and A172 is a well known cell line for Glioblastoma.

Example 3

Figure 1B:
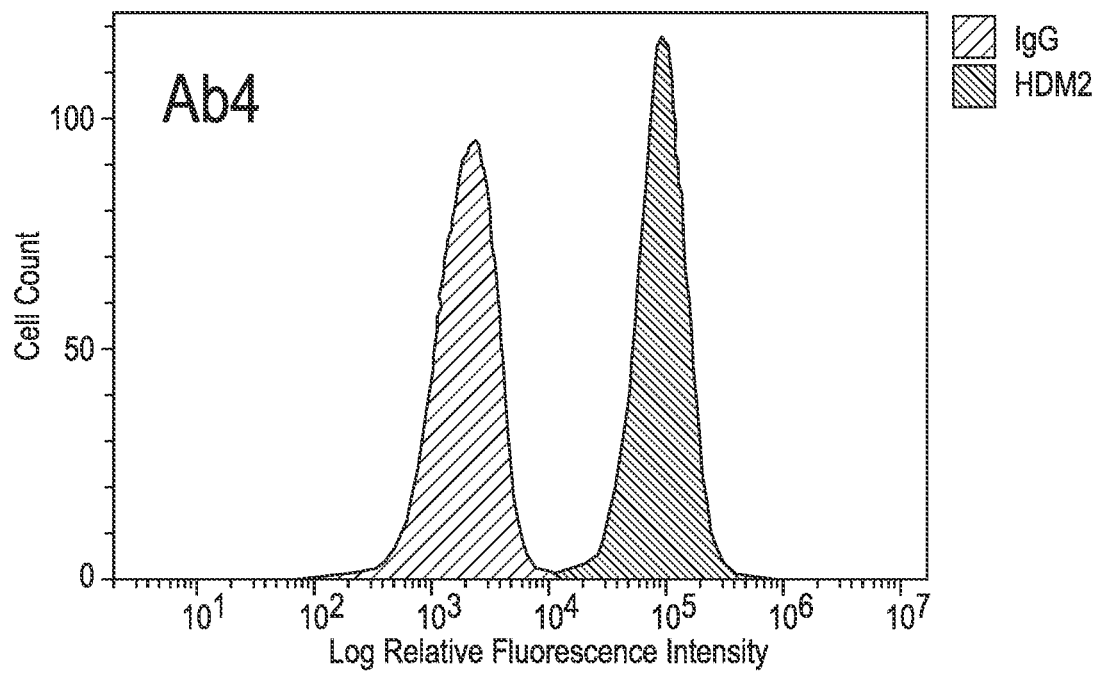

Flow Cytometry was Used to Analyze Two AML Cell Lines (OCI-AML and THP-1)
Flow cytometry was conducted using methods similar to that described in Example 2 and cell surface HDM2 was observed on two AML cell lines (OCI-AML and THP-1). See FIG. 1.

Example 4

Markers for Necrosis and Apoptosis in Cancer Cells Treated with PNC-27 and PNC-28

Cell death can occur by either necrosis or apoptosis. p53-targeting treatments typically cause cell death through apoptosis. Necrosis is not genetically controlled, while apoptosis is genetically controlled. Apoptosis is the deliberate cellular response to specific environmental and developmental stimuli or programmed cell death. Cells undergoing apoptosis exhibit cell shrinkage, membrane blebbing, chromatin condensation and fragmentation. Necrosis involves the destruction of cytoplasmic organelles and a loss of plasma membrane integrity. Though apoptosis does not have the inflammation which results when cancer cells die through necrosis, p53 targeting treatments fail to treat those cancers that do not exhibit p53, or, through mutations, exhibit an inactive p53 form that is unresponsive to p53 targeted treatments. After the DNA damage in the caspase enzyme pathway, there are a series of events which occur that involve calcium activation and calpain enzymes which further leads to other cellular changes and regulation of cytoplasmic enzymes. During p53-dependent apoptosis, there is a sequential expression of annexin V-binding membrane phospho-Serine, Bax wafp21, and caspases; these proteins are used as markers for p53-dependent apoptosis.

A major difference between necrosis and apoptosis in vivo is that in apoptosis there is complete elimination of the apoptotic cell before an immunologic response is seen. Necrosis usually causes immunologic response. Though apoptosis can be thought of as a clean and neat process, the p53 targeting treatments do not result in apoptosis in all types of cancer cases. Though necrosis may typically cause an immunologic response to a treatment site directed at targeting HDM-2, HDM-2-targeting treatments are more effective against various forms of cancer, including those where p53 is not present in the cancer cells, or where p53 is in a mutated or an inactive form.

To determine if PNC-27 or PNC-28 induces cell death by necrosis or by apoptosis, the expression of LDH and caspase in cancer cells treated with PNC-27 or PNC-28 is determined as described above. Early release of LDH (elevation of LDH levels) indicates necrosis. Elevated levels of caspase are indicative of apoptosis Electron micrographs of cancer cells or non-cancerous cells treated with PNC-27 or PNC-28 and untreated cells are performed to determine if the cells exhibit lysis of their plasma membranes or have intact plasma membranes. Lysis of plasma membranes is characteristic of tumor cell necrosis.

Example 5

Transfection of Cancer Cells with a Plasmid that Encodes the p53 Sequence of PNC-27 or PNC-28.

Cancer cells and non-cancerous cells are transfected with empty vector or a green fluorescent protein encoding vector encoding the p53 sequence of PNC-27 or PNC-28. After 2 hours post-transfection, cell counts are performed on slides using light microscopy followed by counting the number of cells exhibiting green fluorescence from GFP (Green Fluorescent Protein). Morphological examination of transfected cells, as visualized by inverted light microscopy is also performed to identify cells that are necrotic or apoptotic.

Cancer cells, for example MiaPaCa-2 cells expressing GFP that are transfected with empty vector a vector expressing the p53 sequence of PNC-27 or PNC-28 are lysed and blotted for p53, wafp21, a protein that is induced by a p53-dependent pathway, and the p53 17-26 peptide itself. In these experiments, the DO-1 anti-p53 antibody that recognizes a determinant that contains residues 17-26 of p53 is used. In addition, caspase activity in these cells is measured. For comparison, the same sets of experiments are performed on cancer cells treated with 0.001-750 μM of PNC-27 or PNC-28. Caspase activity and p53waf21 levels are determined. For controls, actin is blotted for.

In the early stages of apoptosis, phosphatidyl serine (PS), normally present in the inner leaflet of the bilayer membrane of intact cells, is found on the external plasma membrane of cells undergoing apoptosis. Annexin V binds PS and can be located by a probe that carries the red fluorescent TRITC probe. Cells that are transfected with the p53 sequence of PNC-27 or PNC-28 or control vector are processed for staining with Annexin V-biotin followed by streptavidin-TRITC and examined by confocal microscopy. Control experiments with BMRPA1 control cells transfected with a vector expressing the p53 sequence of PNC-27 or PNC-28 or a control vector are also performed and these cells are analyzed for expression of Annexin V.

Example 6

Transfection of Cells with pTracer-SV40 Plasmid Encoding Only the p53 Sequence of PNC-27 or PNC-28

To define the role of the MRP definitively, the effects of the p53 peptide of PNC-27 or PNC-28 itself on tumor cell growth, i.e., whether even without the MRP, it could induce tumor cell necrosis, are determined. The p53 peptide of PNC-27 or PNC-28 is introduced into cancer cells via transfection using the pTracer-SV40 plasmid that constitutively expresses this peptide. The expression of markers for apoptosis and necrosis in the transfected cells are measured and compared with the levels of these markers in replicate samples of cancer cells treated with PNC-27 or PNC-28. These experiments are also performed in BMRPA1 control cells.

Example 7

Induction of Apoptosis in Cancer Cells Treated with the p53 Peptide of PNC-27 or PNC-28

Experiments are performed in cancer cells expressing the p53 peptide of PNC-27 or PNC-28. To determine if apoptosis is occurring, the expression of Wafp21 is determined. Apoptosis is indicated by increased levels of Wafp21. The level of caspase is also determined. An increase in the level of caspase is indicative of apoptosis. The level of expression of annexin-V-binding phosphatidyl serine in the membranes, a known early phenomenon in apoptosis, is determined in cancer cells transfected with the p53 peptide of PNC-27 or PNC-28 as well as cells transfected with empty vector. The level of LDH release is also measured. It is expected that an increase in the release of LDH will occur if the peptide induces tumor cell necrosis.

Example 8

In Vivo Analysis of PNC-27 or PNC-28 Activity

Nu/Nu mice (Harlan Laboratories, Indianapolis, Ind., n=10) weighing 20-22 g, are xenotransplanted subcutaneously (s.c.) with live cancer cells. Tumors are allowed to develop and grow. The following live cancer cells are tested AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous.

After tumor formation has occurred, the mice are separated into three groups. One group of mice receives PNC-27 or PNC-28 and the other group of mice receives PNC-29, a control peptide of similar size, having the following amino acid sequence: MPFSTGKRIMLGE (SEQ ID NO:26). A third group of mice does not receive peptide. The peptides are injected into the mice, a description of dosage protocols are listed below. A total dosage of 1, 10, 20, 30, and 50 mg per mouse is administered over the course of 14 days.

Since the animals are Nu/Nu mice and, thus, immunocompromised they are highly susceptible when exposed to pathogens. Surgery and all preceding and post-surgical treatments are therefore performed in a sterile hood.

Alternatively, using the same methodology as described above, live cancer cells described above ($1 \times 10^6$ cells/mouse) are transplanted to the peritoneal cavity of a group of mice and the compositions disclosed herein are injected in the right shoulder region at the same time of tumor cell transplantation.

Example 9

Cytotoxicity of the Small Molecules of the Present Invention for Cancer Cells

The small molecules of the present invention is incubated with $6 \times 10^6$ cancer cells, for example, Mia-PaCa-2 cells, for 5 days at concentrations ranging from 0.001-750 μM. At different timepoints following treatment the cells are assessed for signs of necrosis, for example, membrane blebbing and disruption and formation of cell clumps coalescing into aggregates of cellular debris. Percent cell death is determined by measuring trypan blue dye uptake. Cancer cells are also treated with the negative control peptide PNC-29 and, separately, a small molecule only having the HDM-2 targeting component that cannot traverse the cell membrane due to the lack of the MRC, administered at the same concentration as the test peptide. The effect of these control peptides on cellular growth, morphology and viability is determined.

As an additional control, the small molecules disclosed herein is combined with untransformed BMRPA1 acinar cells and with the untransformed breast epithelial cell line, MCF-10-2A at a concentration ranging from 0.001-750 μM to determine if the composition is lethal to normal cell growth.

Cell lines for the following cancer cells are tested AML, CLL, CML, Multiple Myeloma, Bile duct, Biliary, Myelodysplastic Syndrome, Polycythemia Vera, Childhood leukemia, Neuroendocrine, Glioblastoma, Astrocytoma, Retinoblastoma, Neuroblastoma, Sarcoma, Uterine cancer, Germ Cell tumor/cancer, Testicular cancer, Wilms tumor, Kidney cancer, Mesothelioma, Liposarcoma, Fibrosarcoma, Fibrous Histiocytoma, Ewings Sarcoma, Burkitts/ALL-BCell, T cell ALL, Non Hodgkins lymphoma, Mantle Cell Lymphoma, Thyroid, Bladder, Head and Neck, Esophageal, Liver, Peritoneal carcinomatosis, Pleural Carcinomatosis, Adrenal, gastrointestinal stromal tumors (GIST), Epidermoid, Plasma Cell, and T cell Lymphoma cutaneous. Cell lines for the aforementioned cancers are well known by those of ordinary skill in the art.

Example 10

Production, Characterization and Humanization of Anti-HDM-2 Monoclonal Antibody

Cells expressing HDM-2 or fragments thereof are produced, and harvested with phosphate buffered saline (PBS) containing 25 mM EDTA and used to immunize BALB/c mice. The mice are given injections i.p. of ~100 cells in 0.5 ml PBS on weeks 0, 2, 5, and 7. The mice with antisera that immunoprecipitated 32P-labeled HDM-2 or fragments thereof are given i.p. injections of a wheat germ agglutinin-Sepharose (WGA) purified HDM-2 membrane extract on weeks 9 and 13. This is followed by an i.v. injection of 0.1 ml of the HDM-2 preparation and the splenocytes are fused with mouse myeloma line X63-Ag8.653. Hybridoma supernatants are screened for HDM-2-binding by ELISA and radioimmunoprecipitation.

The murine monoclonal antibody is humanized, using a "gene conversion mutagenesis" strategy, as described in U.S. Pat. No. 5,821,337, the entire disclosure of which is hereby expressly incorporated by reference.

A small molecule MRC or peptide PRP is conjugated to the antibody as described in Hermanson Bioconjugate Techniques, Third Edition (2013) (ISBN-10: 0123822394).

What is claimed is:

1. A method of treating cancer in a subject in need thereof, comprising:
   i) measuring the amount of a serum biomarker pre-treatment,
   ii) administering to the subject a therapeutically effective amount of a composition comprising a human double minute binding domain (HDM-2) targeting component and a membrane resident component (MRC), and
   iii) measuring the amount of the serum biomarker post-treatment;
   wherein the cancer is acute myeloid leukemia (AML),
   wherein the HDM-2 targeting component is a peptide selected from the group consisting of PPLSQETFSDLWKLL (SEQ ID NO:1) and ETFSDLWKLL (SEQ ID NO:2),
   wherein the MRC is the peptide KKWKMRRNQFWVKVQRG (SEQ ID NO:25),
   wherein the HDM-2 targeting component is attached to the MRC,
   wherein an increase in the amount of the serum biomarker from pre-treatment to post-treatment is indicative of necrosis, membranolysis, or poration of said cancer,
   wherein said composition comprises a peptide of:

PPLSQETFSDLWKLLKKWKMRRNQFWVKVQRG (SEQ ID NO: 48) or

ETFSDLWKLLKKWKMRRNQFWVKVQRG, (SEQ ID NO: 49)

and
   wherein the serum biomarker is cytokeratin.

2. A method of necrosing or causing membranolysis of selective cancer cells, comprising:
   i) providing a plurality of cells in a serum comprising at least one cancer cell and at least one normal cell,
   ii) measuring the amount of a serum biomarker in the serum,
   iii) administering to the plurality of cells a composition comprising a human double minute binding domain (HDM-2) targeting component and a membrane resident component (MRC), and
   iv) measuring the amount of the serum biomarker in the serum after administering the composition,
   wherein administering said composition results in necrosis or membranolysis of said at least one cancer cell, but does not affect said at least one normal cell and an increase in the amount of the serum biomarker from pre-treatment to post-treatment is indicative of necrosis or membranolysis of said cancer cells,
   wherein the at least one cancer cell is an acute myeloid leukemia (AML) cell,
   wherein the HDM-2 targeting component is a peptide selected from the group consisting of PPLSQETFSDLWKLL (SEQ ID NO:1) and ETFSDLWKLL (SEQ ID NO:2),
   wherein the MRC is the peptide KKWKMRRNQFWVKVQRG (SEQ ID NO:25),
   wherein the HDM-2 targeting component is attached to the MRC,
   wherein said composition comprises a peptide of:

PPLSQETFSDLWKLLKKWKMRRNQFWVKVQRG (SEQ ID NO: 48) or

ETFSDLWKLLKKWKMRRNQFWVKVQRG, (SEQ ID NO: 49)

and
   wherein the serum biomarker is cytokeratin.

3. A method of necrosing or causing poration of selective cancer cells, comprising:
   i) providing a plurality of cells in a serum comprising at least one cancer cell and at least one normal cell,
   ii) measuring a level of a serum biomarker,
   iii) administering to the plurality of cells a composition comprising a human double minute binding domain (HDM-2) targeting component and a membrane resident component, and
   iv) measuring the level of the serum biomarker after administering the composition;;

wherein said composition results in necrosis or poration of said cancer cells, but does not affect said normal cells and an increase in the amount of the serum biomarker from pre-treatment to post-treatment of at least two times is indicative of necrosis or poration of said cancer cells, wherein the at least one cancer cell is an acute myeloid leukemia (AML) cell and the HDM-2 targeting component is a peptide selected from the group consisting of PPLSQETFSDLWKLL (SEQ ID NO:1) and ETFSDLWKLL (SEQ ID NO:2), wherein the MRC is the peptide KKWKMRRNQFWVKVQRG (SEQ ID NO:25), wherein the HDM-2 targeting component is attached to the MRC, wherein said composition comprises a peptide of:

```
                                        (SEQ ID NO: 48)
PPLSQETFSDLWKLLKKWKMRRNQFWVKVQRG
or
                                        (SEQ ID NO: 49)
ETFSDLWKLLKKWKMRRNQFWVKVQRG,
``` and wherein the serum biomarker is cytokeratin.

4. A method of necrosing, causing poration, or causing membranolysis of an acute myeloid leukemia (AML) cell in a serum, said method comprising:

i) measuring a level of a serum biomarker, ii) administering to a plurality of cells a peptide having a sequence of

```
                                        (SEQ ID NO: 48)
PPLSQETFSDLWKLLKKWKMRRNQFWVKVQRG or
                                        (SEQ ID NO: 49)
ETFSDLWKLLKKWKMRRNQFWVKVQRG,
``` iii) measuring the level of the serum biomarker after administering the peptide;

wherein the plurality of cells include at least one normal cell and one AML cell, wherein an increase in the amount of the serum biomarker from pre-treatment to post-treatment is indicative of necrosis, membranolysis, or poration of said AML cell, wherein said composition comprises a peptide of:

```
                                        (SEQ ID NO: 48)
PPLSQETFSDLWKLLKKWKMRRNQFWVKVQRG or
                                        (SEQ ID NO: 49)
ETFSDLWKLLKKWKMRRNQFWVKVQRG,
``` and wherein the serum biomarker is cytokeratin.

* * * * *